(12) United States Patent
Wolinsky et al.

(10) Patent No.: US 6,533,807 B2
(45) Date of Patent: *Mar. 18, 2003

(54) RADIALLY-EXPANDABLE STENT AND DELIVERY SYSTEM

(75) Inventors: Lone Wolinsky, Ramat Gan (IL); Ofer Nativ, Rishon Lezion (IL); Amir Loshakove, Moshav Burgata (IL)

(73) Assignee: Medtronic, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/019,210

(22) Filed: Feb. 5, 1998

(65) Prior Publication Data

US 2001/0044648 A1 Nov. 22, 2001

(51) Int. Cl.$^7$ .................................................. A61F 2/06
(52) U.S. Cl. ...................................... 623/1.15; 623/1.18
(58) Field of Search .............................. 623/1.1, 1.11, 623/1.12, 1.13, 1.14, 1.15, 1.16, 1.17, 1.18, 1.19; 606/194

(56) References Cited

U.S. PATENT DOCUMENTS

| 4,553,545 | A | 11/1985 | Maass et al. ............... 128/341 |
| 4,649,922 | A | 3/1987 | Wiktor ........................ 128/344 |
| 4,655,771 | A | 4/1987 | Wallsten ........................ 623/1 |
| 4,732,152 | A | 3/1988 | Wallsten et al. ............ 128/343 |
| 4,760,849 | A | 8/1988 | Kropf .......................... 128/341 |
| 4,768,507 | A | 9/1988 | Fischell et al. ............. 128/303 |
| 4,830,003 | A | 5/1989 | Wolff et al. ................. 128/343 |
| 4,878,906 | A | 11/1989 | Lindemann et al. ........... 623/1 |
| 4,886,062 | A | 12/1989 | Wiktor et al. ............... 128/343 |
| 4,954,126 | A | 9/1990 | Wallsten ....................... 600/36 |
| 4,969,458 | A | 11/1990 | Wiktor ........................ 606/194 |
| 4,990,151 | A | 2/1991 | Walsten ....................... 606/108 |
| 5,026,377 | A | 6/1991 | Burton et al. ................ 606/108 |
| 5,035,706 | A | 7/1991 | Giantureo et al. ........... 606/198 |
| 5,078,720 | A | 1/1992 | Burton et al. ................ 606/108 |

(List continued on next page.)

FOREIGN PATENT DOCUMENTS

| EP | 0 818 184 A1 | 1/1998 | |
| WO | WO 94/15549 | 7/1994 | |
| WO | 95/31945 | 11/1995 | ............. A61F/2/06 |
| WO | 9626689 | * 6/1996 | ................ 623/1.15 |
| WO | 96/26689 | 9/1996 | ............. A61F/2/06 |
| WO | WO 96/41592 | 12/1996 | |
| WO | WO 97/21399 | 6/1997 | |

*Primary Examiner*—Corrine McDermott
*Assistant Examiner*—A. Stewart
(74) *Attorney, Agent, or Firm*—Mueting, Raasch & Gebhardt, P.A.

(57) ABSTRACT

The present invention provides radially-expandable stents that, in various embodiments, may reduce the bending stresses/strains associated with the compressed state of self-expanding stents and/or may prevent longitudinal expansion/contraction of radially expandable stents between the compressed and expanded states. In addition, stents according to the present invention preferably exhibit increased longitudinal flexibility in both the compressed and expanded states. The present invention also includes delivery systems in which threading of the guidewire through the delivery system may be simplified. In addition, the delivery systems according to the present invention may also incorporate a balloon to assist in radially expanding the stent and/or seating of the stent in the lumen during deployment without removing the stent delivery catheter. Further, the delivery systems may also include a support tube at the proximal end to assist in fixing the position of the stent relative to a guide catheter during deployment of the stent.

14 Claims, 8 Drawing Sheets

U.S. PATENT DOCUMENTS

| | | | |
|---|---|---|---|
| 5,158,548 A | 10/1992 | Lau et al. | 604/96 |
| 5,160,341 A | 11/1992 | Brenneman et al. | 606/198 |
| 5,192,297 A | 3/1993 | Hull | 606/195 |
| 5,201,757 A | 4/1993 | Heyn et al. | 606/198 |
| 5,242,399 A | 9/1993 | Lau et al. | 604/104 |
| 5,246,445 A | 9/1993 | Yachia et al. | |
| 5,275,622 A | 1/1994 | Lazarus et al. | 623/1 |
| 5,290,295 A | 3/1994 | Querals et al. | 606/108 |
| 5,344,426 A | 9/1994 | Lau et al. | 606/198 |
| 5,356,423 A | 10/1994 | Tihon et al. | 606/194 |
| 5,372,600 A | 12/1994 | Beyar et al. | |
| 5,389,106 A * | 2/1995 | Tower | 606/198 |
| 5,397,345 A | 3/1995 | Lazarus | 623/1 |
| 5,405,377 A | 4/1995 | Cragg | 623/1 |
| 5,405,378 A | 4/1995 | Strecker | 623/1 |
| 5,411,551 A | 5/1995 | Winston et al. | 623/1 |
| 5,415,664 A | 5/1995 | Pinchuk | 606/108 |
| 5,443,496 A | 8/1995 | Schwartz et al. | 623/1 |
| 5,445,646 A | 8/1995 | Euteneuer et al. | 606/198 |
| 5,474,563 A | 12/1995 | Myler et al. | 606/108 |
| 5,476,505 A | 12/1995 | Limon | 623/1 |
| 5,480,423 A | 1/1996 | Ravenscroft et al. | 623/1 |
| 5,507,767 A | 4/1996 | Maeda et al. | |
| 4,954,126 A | 5/1996 | Wallsten | 600/36 |
| 5,514,154 A | 5/1996 | Lau et al. | |
| 5,522,882 A | 6/1996 | Gaterud et al. | 623/1 |
| 5,534,007 A | 7/1996 | St. Germain et al. | 606/108 |
| 5,540,712 A | 7/1996 | Kleshinski et al. | 606/198 |
| 5,545,208 A | 8/1996 | Wolff et al. | 623/1 |
| 4,655,771 A | 9/1996 | Wallsten | 623/1 |
| 5,554,181 A | 9/1996 | Das | 623/1 |
| 5,556,413 A | 9/1996 | Lam | 606/198 |
| 5,562,697 A * | 10/1996 | Christiansen | 606/191 |
| 5,571,135 A | 11/1996 | Fraser et al. | 606/198 |
| 5,571,168 A | 11/1996 | Toro | 623/1 |
| 5,591,172 A | 1/1997 | Bachmann et al. | 606/108 |
| 5,591,230 A | 1/1997 | Horn et al. | |
| 5,593,442 A | 1/1997 | Klein | 623/12 |
| 5,597,378 A | 1/1997 | Jervis | 606/78 |
| 5,601,593 A | 2/1997 | Freitag | |
| 5,603,698 A | 2/1997 | Roberts et al. | 604/104 |
| 5,607,466 A | 3/1997 | Imbert et al. | 623/1 |
| 5,618,301 A | 4/1997 | Hauenstein et al. | |
| 5,634,928 A | 6/1997 | Fischell et al. | 606/108 |
| 5,639,274 A | 6/1997 | Fischell et al. | 604/96 |
| 5,662,703 A | 9/1997 | Yurek et al. | 623/1 |
| 5,662,713 A | 9/1997 | Anderson et al. | 623/12 |
| 5,669,932 A | 9/1997 | Fischell et al. | 606/198 |
| 5,681,322 A | 10/1997 | Hartigan, Jr. | 606/108 |
| 5,683,448 A | 11/1997 | Cragg | 623/1 |
| 5,683,451 A | 11/1997 | Lenker et al. | 623/1 |
| 5,707,387 A | 1/1998 | Wijay | |
| 5,716,393 A * | 2/1998 | Lindenberg et al. | 623/1 |
| 5,733,325 A | 3/1998 | Robinson et al. | |
| 5,776,161 A * | 7/1998 | Globerman | 606/194 |
| 5,800,456 A | 9/1998 | Maeda et al. | |
| 5,800,515 A * | 9/1998 | Nadal et al. | 623/1 |
| 5,800,526 A | 9/1998 | Anderson et al. | |
| 5,807,404 A | 9/1998 | Richter | |
| 5,814,063 A | 9/1998 | Freitag | |
| 5,827,321 A | 10/1998 | Roubin et al. | |
| 5,861,027 A * | 1/1999 | Trapp | 623/1 |
| 5,968,093 A | 10/1999 | Kranz | |
| 6,010,530 A | 1/2000 | Goicoechea | |
| 6,017,365 A | 1/2000 | Von Oepen | |
| 6,033,433 A * | 3/2000 | Ehr et al. | 623/1 |
| 6,042,606 A | 3/2000 | Frantzen | |
| 6,090,127 A | 7/2000 | Globerman | |
| 6,106,548 A | 8/2000 | Roubin et al. | |
| 6,165,210 A | 12/2000 | Lau et al. | |

* cited by examiner

RADIALLY-EXPANDABLE STENT AND DELIVERY SYSTEM

FIELD OF THE INVENTION

The present invention relates to intravascular stent implants for maintaining vascular patency in humans and animals. More particularly, the present invention provides a radially-expandable stent and a delivery system for delivering a radially-expandable stent within a body lumen.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen.

The dilatation of the occlusion, however, can form flaps, fissures and dissections which threaten reclosure of the dilated vessel or even perforations in the vessel wall. Implantation of a stent can provide support for such flaps and dissections and thereby prevent reclosure of the vessel or provide a patch repair for a perforated vessel wall until corrective surgery can be performed. It has also been shown that the use of intravascular stents can measurably decrease the incidence of restenosis after angioplasty thereby reducing the likelihood that a secondary angioplasty procedure or a surgical bypass operation will be necessary.

An implanted prosthesis such as a stent can preclude additional procedures and maintain vascular patency by mechanically supporting dilated vessels to prevent vessel reclosure. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

A typical stent is a cylindrically shaped wire formed device intended to act as a permanent prosthesis. A typical stent ranges from 5 mm to 50 mm in length. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. The stent expands radially as the balloon is inflated, forcing the stent into contact with the interior of the body lumen thereby forming a supporting relationship with the vessel walls.

Conventional angioplasty balloons fall into high, medium and low pressure ranges. Low pressure balloons are those which fall into rated burst pressures below 6 atmospheres. Medium pressure balloons are those which fall into rated burst pressures between 6 and 12 atmospheres. High pressure balloons are those which fall into rated burst pressures above 12 atmospheres. Burst pressure is determined by material selection, wall thickness and tensile strength.

The biocompatible metal stent props open blocked coronary arteries, keeping them from reclosing after balloon angioplasty. A balloon of appropriate size and pressure is first used to open the lesion. The process is repeated with a stent crimped on a second balloon. The second balloon may be a high pressure type of balloon, e.g., more than 12 atmospheres, to insure that the stent is fully deployed upon inflation. The stent is deployed when the balloon is inflated. The stent remains as a permanent scaffold after the balloon is withdrawn. A high pressure balloon is preferable for stent deployment because the stent must be forced against the artery's interior wall so that it will fully expand thereby precluding the ends of the stent from hanging down into the channel encouraging the formation of thrombus.

Various shapes of stents are known in the art. U.S. Pat. No. 4,649,922 (Wiktor) discloses a linearly expandable spring-like stent. U.S. Pat. No. 4,886,062 (Wiktor) discloses a two-dimensional zigzag form, typically a sinusoidal form. U.S. Pat. No. 4,969,458 (Wiktor) discloses a stent wire coiled into a limited number of turns wound in one direction, then reversed and wound in the opposite direction with the same number of turns, then reversed again and so on until a desired length is obtained.

Stents have limited ability to provide effective patching of perforated vessels due to the spacing between metal elements. U.S. Pat. No. 4,878,906 (Lindeman et al.) describes an endoprosthesis made of a thin wall molded plastic sleeve intended to be collapsed radially and delivered to a damaged area of a vessel where it is expanded to provide a sealed interface to the vessel on its outer peripheral ends. The endoprosthesis therefore provides a patch which prevents leakage of blood from a vessel wall. The endoprosthesis disclosed employs various molded-in ribs, struts and the like to adapt the device for particular applications and to provide the desired degree of stiffness to form the sealed interface with the vessel wall. Such a stiff prosthesis, however, could not be expected to have the longitudinal flexibility needed to adapt to curved vessels.

One problem with self-expanding stents is that the stents must be compressed into a small diameter for delivery to the site or portion of the body lumen at which support is desired. It is preferable that the stents be compressed into as small of a diameter as possible (typically referred to as "profile") to assist in delivering the stent to the desired site. That compression can, in some cases cause localized areas of high bending stress/strain within the stent.

As a result of the high bending stresses/strain, the minimum profile for the self-expanding stents can be limited to prevent non-recoverable strain levels in the stent and, therefore, ensure full radial expansion of the stent when released from the delivery system. The larger profile can limit the delivery and use of the stent to larger diameter lumens.

Alternatively, if a small delivery profile is desired, then the stent may be designed to achieve that profile which can often result in a larger window area and a reduction in the outward forces generated by the stent after expansion within the lumen. The larger window area and, therefore, inferior body lumen scaffolding reduces the effectiveness against recurring restenosis. The reduced outward forces may be problematic if the stent does not firmly engage the wall of the lumen.

One attempt at addressing the high bending stresses/strains in a self-expanding stent is described in U.S. Pat. No. 4,830,003 (Wolff et al.) in which the stent is made of a series of generally straight wire segments welded together at their ends to form a zigzag shaped stent when expanded. By using generally straight wires, the bending stresses/strains associated with bends in an integral wire-formed stent body can be avoided. Disadvantages associated with this approach include, however, the cost of manufacturing the stents by welding. The welds also lower the allowable stress levels in the stent, thereby limiting its fatigue life and compression for delivery. Another disadvantage is that the length of the stent can change significantly from the compressed state to the expanded state, thereby making accurate placement of the stent at the desired location within a body lumen more difficult.

Another attempt at addressing the high bending stresses/strains includes manufacturing self-expanding stents from materials other than metals as described in, e.g., U.S. Pat. No. 5,356,423 (Tihon et al.). The stents disclosed therein are formed of thermoplastic materials and can be molded or otherwise formed into a fenestrated pattern similar to those produced by braided wire stents. By shaping the openings as depicted in FIG. 5 of the patent, the stress concentration at the bending points can be reduced. Disadvantages of this approach include, however, degradation associated with implanted plastic materials, including changes in the elasticity of the plastics which can result in a reduction in the radially outward forces generated by the stent.

SUMMARY OF THE INVENTION

It is an object of the invention to provide a self-expanding stent for implantation within a body lumen that provides for reductions in the bending stresses/strains associated with compression of the stent for delivery to the desired location within a body lumen.

It is another object of the present invention to provide a self-expanding stent in which the longitudinal length of the stent remains unchanged from the compressed state to the expanded state.

It is a further object of the invention to provide a stent with improved longitudinal flexibility to allow for threading through tortuous lumens and lesions, as well as to permit implantation in highly curved lumens.

It is an object of some delivery systems according to the present invention to provide a delivery system in which the position of the stent can be fixed relative to a guide catheter.

It is another object of some delivery systems according to the present invention to provide a balloon integral with the stent delivery device to allow for post-deployment dilatation of the stent without removing the stent delivery catheter.

It is another object of some delivery systems of the present invention to provide for simplified threading of a guidewire through a distal portion of a rapid-exchange delivery system.

In one aspect, the present invention provides radially expandable stent for implantation within a body lumen including an elongated generally tubular body defining a passageway having a longitudinal axis; the body including a plurality of circumferential support sections arranged successively along the longitudinal axis, each of the support sections having a length along the longitudinal axis; each of the circumferential support sections including a plurality of primary bends interconnected by struts, the primary bends being located on alternating ends of the support section around the circumference of the body, each of the struts connecting successive primary bends on opposite ends of the support section and having a midpoint generally located therebetween; and at least one longitudinal member connecting adjacent support sections in the body, the longitudinal member having a first end attached proximate the midpoint of one of the struts and a second end attached proximate the midpoint of one of the struts in the adjacent support section; wherein the stent is radially compressible into a compressed state in which the struts are generally aligned with the longitudinal axis and radially expandable into an expanded state in which the struts and the primary bends in each of the support sections are arranged in a zigzag pattern, and further wherein the longitudinal length of the stent in the compressed state is substantially the same as the longitudinal length of the stent in the expanded state.

In another aspect the present invention provides a self-expanding radially expandable stent for implantation within a body lumen including an elongated generally tubular body defining a passageway having a longitudinal axis, the body including at least one circumferential support section having a length along the longitudinal axis; each of the circumferential support sections including a plurality of primary bends interconnected by struts, the primary bends being located on alternating ends of the support section around the circumference of the body, each of the struts connecting successive primary bends on opposite ends of the support section and having a midpoint generally located therebetween; wherein the stent is radially compressible into a compressed state and radially expandable into an expanded state in which the struts and primary bends in each of the support sections are arranged in a zigzag pattern, and further wherein each pair of adjacent struts associated with each of the primary bends abut at a point between the primary bend and the midpoint of each strut in the pair of adjacent struts when the stent is in the compressed state, whereby the bending stress is reduced at each primary bend of the plurality of primary bends.

In another aspect, the present invention provides a self-expanding radially expandable stent for implantation within a body lumen including an elongated generally tubular body defining a passageway having a longitudinal axis, the body including at least one circumferential support section having a length along the longitudinal axis; each of the circumferential support sections including a substantially continuous element including a plurality of primary bends interconnected by struts, the primary bends being located on alternating ends of the support section around the circumference of the body, each of the struts connecting successive primary bends on opposite ends of the support section and having a midpoint generally located therebetween, wherein the stent is radially compressible into a compressed state and radially expandable into an expanded state in which the struts and primary bends in each of the support sections are arranged in a zigzag pattern; and means for reducing bending stress at the primary bends when the stent is in the compressed state.

In another aspect, the present invention provides a delivery system for implantation of a radially-expandable stent within a body lumen including an inner tube having a proximal end and a distal end, the inner tube having an inner tube lumen formed therein, the inner tube lumen having an opening at the distal end of the inner tube; a cover sheath having a proximal end and a distal end, the cover sheath comprising a wall defining a cover sheath lumen, the inner tube located within the cover sheath lumen; a stent positioned about the inner tube at the distal end of the cover sheath; a first guidewire opening in the inner tube lumen, the first guidewire opening spaced from the distal end of the inner tube; a second guidewire opening in the wall of the cover sheath, the second guidewire opening located proximate the first guidewire opening; and a guide element having a distal end located within the inner tube lumen, the guide element extending between the first and second guidewire openings.

In another aspect, the present invention provides a method of deploying a stent within a body lumen by providing a radially expandable stent on a delivery system including an inner tube having a proximal end and a distal end, the inner tube having an inner tube lumen formed therein, the inner tube lumen having an opening at the distal end of the inner tube and a first guidewire opening in the inner tube lumen, the first guidewire opening spaced from the distal end of the inner tube; a stent positioned on the exterior surface of the inner tube at the distal end of the inner tube; a cover sheath having a proximal end and a distal end, the cover sheath comprising a wall defining a cover sheath lumen, the inner tube and stent located within the cover sheath lumen, the cover sheath further including a second guidewire opening in the wall of the cover sheath, the second guidewire opening located proximate the first guidewire opening in the inner tube; and a guide element having a distal end located within the inner tube lumen, the guide element extending between the first and second guidewire openings, wherein the guide element comprises a guide lumen formed in the distal end of the guide element; positioning a guidewire within a body lumen, wherein a proximal end of the guidewire extends out of the body lumen; inserting the proximal end of the guidewire into the inner tube lumen at the distal end of the inner tube; advancing the proximal end of the guidewire through the inner tube lumen towards the first guidewire opening and the distal end of the guide element, wherein at least a portion of the proximal end of the guidewire is advanced into the guide lumen in the distal end of the guide element; advancing the proximal end of the guidewire through the first and second guidewire openings; advancing the distal end of the inner tube and the stent over the guidewire towards the distal end of the guidewire, wherein the stent is positioned at a desired location within the body lumen; and deploying the stent at the desired location within the body lumen.

In another aspect, the present invention provides a method of deploying a stent within a body lumen by providing a radially expandable stent on a delivery system including an inner tube having a proximal end and a distal end, the inner tube having an inner tube lumen formed therein; a stent positioned on the exterior surface of the inner tube at the distal end of the inner tube; an expandable balloon located on the inner tube; an inflation lumen in fluid communication with the balloon, the inflation lumen extending from the proximal end of the delivery system to the balloon; and a cover sheath having a proximal end and a distal end, the cover sheath comprising a wall defining a cover sheath lumen, the inner tube, stent, and balloon located within the cover sheath lumen; positioning the inner tube, stent, balloon and cover sheath within a body lumen; moving the cover sheath proximally relative to the distal end of the inner tube to deploy the stent with the body lumen; and inflating the balloon within the stent.

In another aspect, the present invention provides a method of deploying a stent within a body lumen by providing a radially expandable stent on a delivery system including an inner tube having a proximal end and a distal end; a stent positioned on the exterior surface of the inner tube at the distal end of the inner tube; a cover sheath having a proximal end and a distal end, the cover sheath including a cover sheath lumen, the inner tube and stent located within the cover sheath lumen; and a support tube having a proximal end and a distal end, the support tube including a support tube lumen containing at least a portion of the proximal end of the cover sheath, the cover sheath being movable in the proximal and distal directions within the support tube lumen and the position of the inner tube being fixed relative to the position of the support tube; positioning a guide catheter within a body lumen; advancing the distal ends of the inner tube and the cover sheath through the guide catheter; fixing the position of the support tube relative to the guide catheter, wherein the positions of the distal end of the inner tube and the stent within the body lumen are also fixed relative to the guide catheter; and moving the cover sheath proximally to release the stent on the distal end of the inner tube, thereby deploying the stent within the body lumen.

These and other features and advantages of the present invention are described below in connection the description of the preferred embodiments.

DETAILED DESCRIPTION OF THE PREFERRED EMBODIMENTS

The present invention includes radially-expandable stents that, in various embodiments, may reduce the bending stresses/strains associated with the compressed state of self-expanding stents and/or may prevent longitudinal expansion/contraction of radially expandable stents between the compressed and expanded states. In addition, stents according to the present invention preferably exhibit increased longitudinal flexibility in both the compressed and expanded states.

The present invention also includes delivery systems in which threading of the guidewire through the delivery system may be simplified. In addition, the delivery systems according to the present invention may also incorporate a balloon to assist in radially expanding the stent and/or seating of the stent in the lumen during deployment without removing the stent delivery catheter. Further, the delivery systems may also include a support tube at the proximal end to assist in fixing the position of the stent relative to a guide catheter during deployment of the stent.

Although the following discussion, along with the figures, describes illustrative preferred embodiments and methods according to the present invention, those skilled in the art will understand that other structures and/or methods could also be used to accomplish the desired functions. For example, although stents having one or more support sections are described herein, it will be understood that stents manufactured according to the present invention could have any number of desired support sections needed to obtain a stent with a desired longitudinal length. Furthermore, it will be understood that the figures are schematic only, and that the relative dimensions of the various illustrated features are not intended to limit the scope of the present invention.

Figure 1:
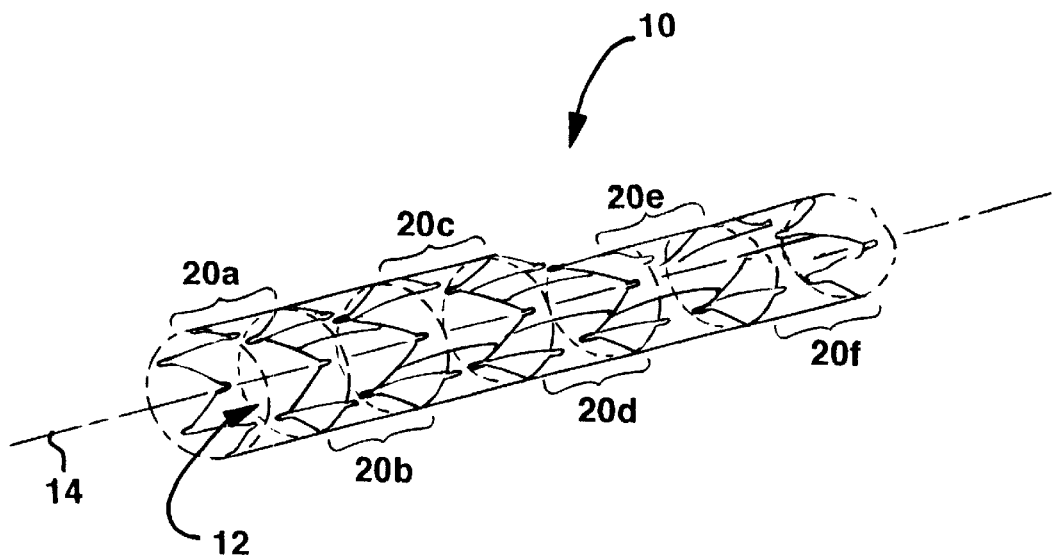
FIG. 1 is a perspective view of one radially expanded stent according to the present invention.

FIG. 1 depicts one illustrative self-expanding stent according to the present invention. The depicted stent includes a generally tubular body 10 defining a passageway 12 extending along a longitudinal axis 14. The body 10 is preferably formed from a plurality of support sections 20a, 20b, 20c, 20d, 20e, and 20f (collectively referred to as support sections 20 below) arranged successively along the longitudinal axis 14. The body 10 is depicted in FIG. 1 in its expanded state in which the support sections 20 have been expanded radially outward from the longitudinal axis 14.

Figure 2:
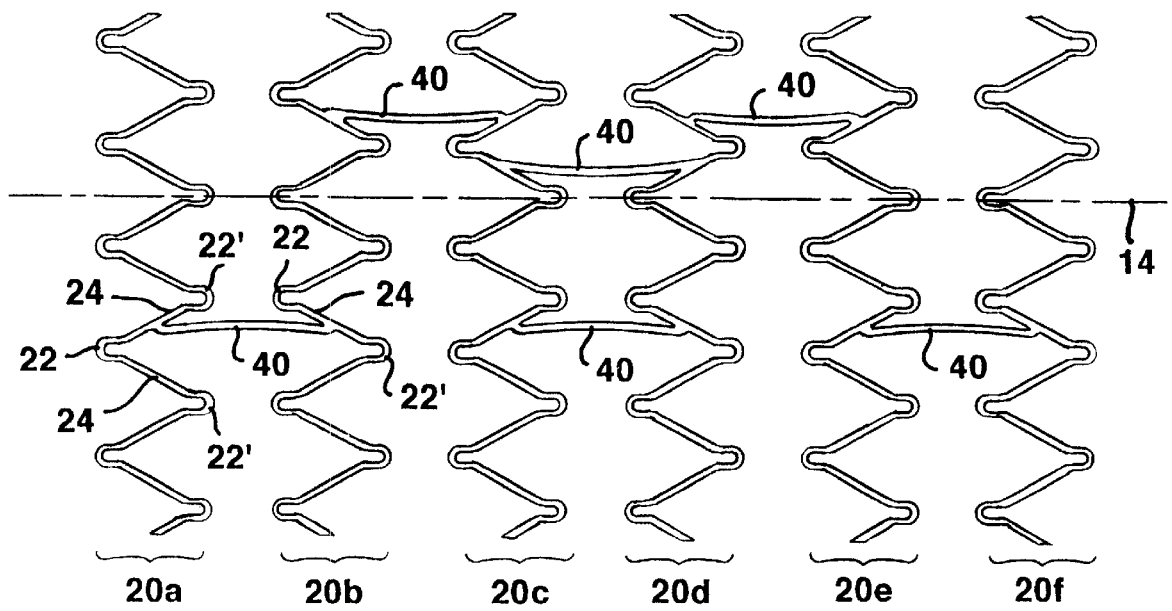
FIG. 2 is a plan view of the stent of FIG. 1 in which the body of the stent is unrolled.

FIG. 2 is a plan view of a portion of the body 10 of the stent depicted in FIG. 1 in which the body has been unrolled from the tubular shape of FIG. 1. Each of the support sections 20 is depicted and has a length along the longitudinal axis 14. Referring specifically to support section 20a, the support section 20a includes a plurality of primary bends 22 and 22' located on alternating ends of the support section 20a. Primary bend 22 on one end of the support section 20a is connected to a primary bend 22' by a strut 24. Because of the alternating nature of the primary bends 22 and 22', the primary bends 22/22' and struts 24 are arranged in a zigzag pattern when the stent is in the expanded state (as in FIGS. 1 and 2).

Adjacent support sections 20a and 20b are connected to each other by at least one longitudinal member 40 extending between the support sections 20a and 20b. It is preferred that the longitudinal members 40 are attached to the struts 24, although they may be attached at any location on each of the support sections 20. More preferably, the longitudinal members 40 are attached to the struts 24 at the midpoint of the length of the struts 24 between the primary bends 22 and 22'. By attaching the longitudinal members 40 at the midpoints of the struts, the length of the body 10 of the stent along the longitudinal axis 14 will exhibit substantially no change between the compressed state and the expanded state.

Although most of the adjacent support sections 20 are connected by only one longitudinal member 40 in FIG. 2, it should be noted that a plurality of longitudinal members 40 can be used to connect the support sections 20. For example, support sections 20c and 20d are connected by two longitudinal members 40 in FIG. 2. Where more than one longitudinal member 40 is used to connect adjacent support sections 20, it is preferred that the longitudinal members be spaced evenly about the circumference of the body 10. For example, where two longitudinal members 40 are provided, it is preferred that they be located about 180 degrees apart, three longitudinal members 40 would preferably be located about 120 degrees apart, etc.

It may be preferred (but not required) that smaller stents, i.e., those having a diameter as manufactured of about 6 millimeters or less, employ two or more longitudinal members 40 to connect adjacent support sections 20. It may also be preferred (but not required) that larger stents, i.e., those having manufactured diameters of about 5 millimeters or more, employ three or more longitudinal members 40 to connect adjacent support sections 20. The exact number of longitudinal members used in any stent according to the present invention will, however, vary based on the need for longitudinal flexibility.

It is preferred that the longitudinal members 40 connecting immediately adjacent support sections 20 are not aligned along the longitudinal axis 14 of the stent. As one example of this, the arrangement of the longitudinal members 40 in the first three support sections 20a, 20b, and 20c can be described. As can be seen in FIG. 2, the longitudinal members 40 connecting support sections 20a and 20b are not aligned along the longitudinal axis 14 with the longitudinal members 40 connecting support sections 20b and 20c. It is generally preferred that the longitudinal members connecting, e.g., support sections 20a and 20b, be tangentially out of phase from longitudinal members 40 connecting support sections 20b and 20c by as large an amount as possible. For example, if the support sections 20a, 20b and 20c are all connected to their adjacent support sections 20 by two longitudinal members 180 degrees apart, it is preferred that the longitudinal members 40 connecting support sections 20a and 20b be tangentially out of phase by 90 degrees from the longitudinal members 40 connecting the support sections 20b and 20c.

Providing longitudinal members 40 connecting immediately adjacent support sections 20, e.g., 20a and 20b, circumferentially spaced about the support sections 20 can improve the flexibility of the body 10 along the longitudinal axis 14. In addition, providing the longitudinal members 40 tangentially out of phase along the length of the body 10, e.g., between sections 20a–20b and 20b–20c, can also improve the longitudinal flexibility of stents according to the present invention. Although these concepts have been described with reference to three successive support sections, it will be understood that these concepts can be extended along the entire length of a stent incorporating as few as two support sections and as many support sections as desired.

It is significant to note that the longitudinal bending flexibility is improved both when the stent is in the compressed state during delivery and upon deployment of the stent in a body lumen. Increased longitudinal bending flexibility when compressed permits threading of the stent through long tortuous vessels and lesions. Increased longitudinal bending flexibility when expanded allows for deployment in highly curved vessels or lumens.

It will be understood that the longitudinal members 40 described above may be incorporated into self-expanding stents or into stents that are not self-expanding, i.e., stents that must be expanded by a balloon or some other method. In addition, the connection of the longitudinal members 40 can be used in any stent providing zigzag support sections, whether the stent includes primary bends such as those described herein or not. In any case, the connection of the longitudinal members 40 the midpoints of the struts 24 in adjacent zigzag support sections 20 will prevent changes in the longitudinal length of stents incorporating zigzag support sections similar to those described herein.

Figure 3:
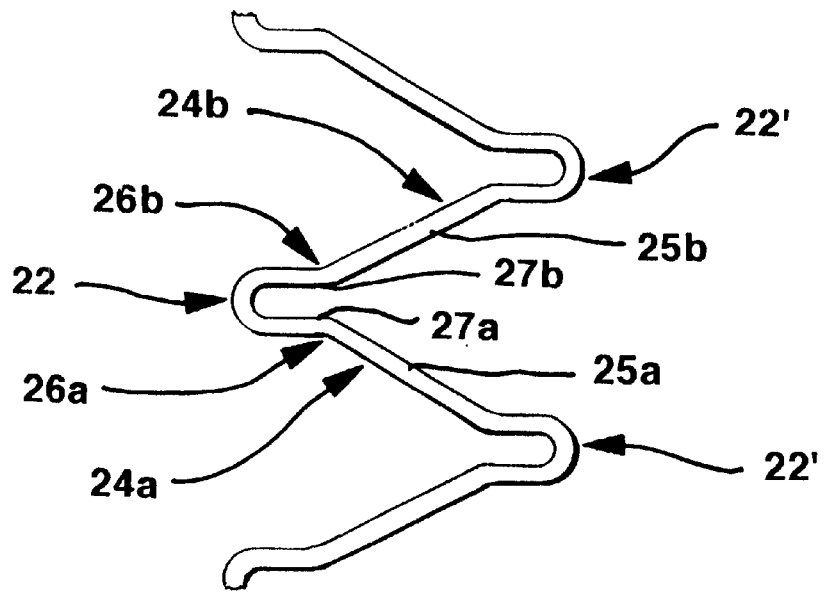
FIG. 3 is an enlarged partial view of the stent body of FIG. 2 in the expanded state.

FIG. 3 is an enlarged view of a portion of the one of the support sections 20 in FIG. 2. A primary bend 22 is shown along with two opposing primary bends 22' on the opposite end of the support section. The primary bend 22 is attached to a pair of struts 24a and 24b. The lower strut 24a is attached to the lower opposing primary bend 22' while the upper strut 24b is attached to the upper opposing primary bend 22'. Strut 24a has a midpoint 25a that is generally located midway between the primary bend 22 and the lower opposing primary bend 22' while strut 24b has a midpoint 25b that is generally located midway between the primary bend 22 and the upper opposing primary bend 22'.

Strut 24a includes a secondary bend 26a located between its midpoint 25a and the primary bend 22. The secondary bend 26a forms an apex 27a facing the other strut 24b attached to the primary bend 22. Strut 24b includes a secondary bend 26b located between its midpoint 25b and the primary bend 22. The secondary bend 26b forms an apex 27b facing the other strut 24a attached to the primary bend 22. As depicted in FIGS. 2 and 3, it is preferred that each of the struts 24 connecting primary bends 22 and 22' include two secondary bends, with one secondary bend being located on each side of the midpoint of the strut 24.

Figure 4:
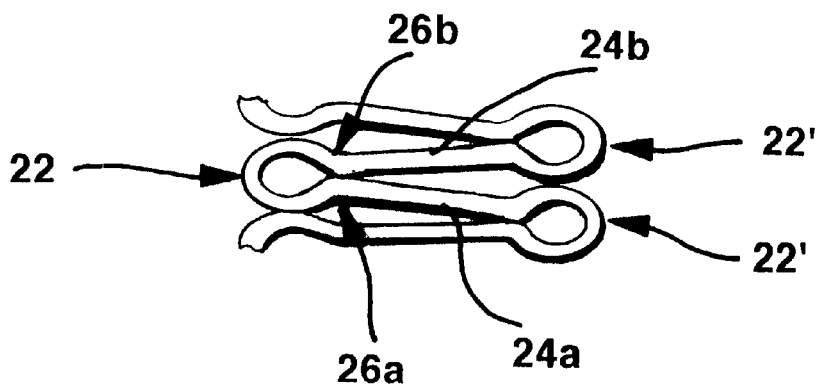
FIG. 4 is an enlarged partial view of the stent body of FIG. 2 in the compressed state.

FIG. 4 depicts the portion of the support section of FIG. 3 in the compressed state in which the opposing upper and lower primary bends 22' are moved together. As a result, the struts 24a and 24b are also moved together, and abut each other first at a point between the midpoints 25a and 25b of the respective struts 24a and 24b. In the embodiment depicted in FIGS. 3 and 4, the point at which the struts associated with or attached to the primary bend 22 abut first is at the apexes 27a and 27b of the struts 24a and 24b. As a result, the minimum radius formed by the primary bend 22 during compression of the stent is limited by the abutting relationship of the apexes 27a and 27b that redistributes the stresses associated with compression of the stent into the struts 24a and 24b.

Figure 5:
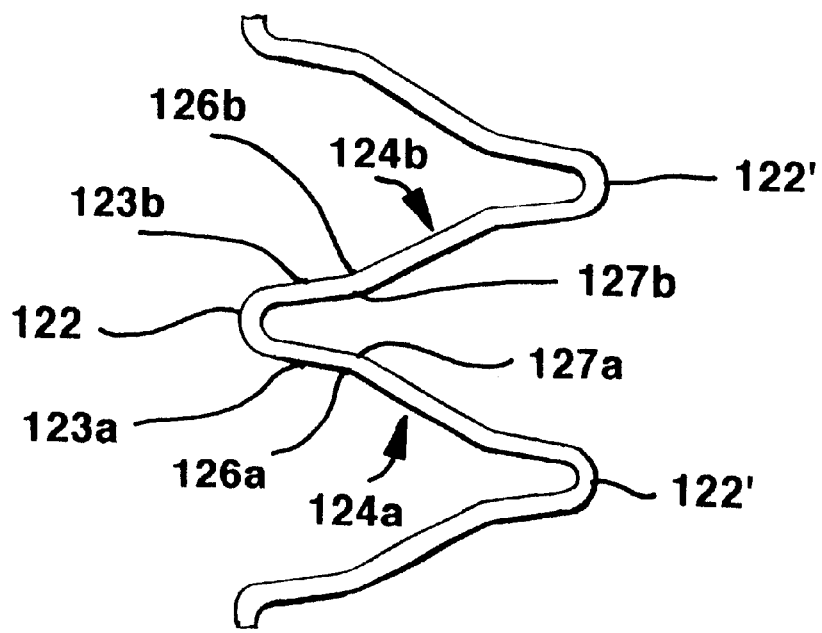
FIGS. 5–8 are enlarged partial views of portions of alternative stents according to the present invention.

The construction of the supports sections depicted in FIGS. 2–4 can be modified while still limiting the maximum stresses associated with compression of the stent. One alternative is depicted in FIG. 5 and includes a primary bend 122 on one end of a support section and two opposing primary bends 122' on the opposing end of the support section. The strut 124a connecting the primary bend 122 with the lower opposing primary bend 122' includes a secondary bend 126a and the strut 124b connecting the primary bend 122 with the upper opposing primary bend 122' includes a secondary bend 126b.

The primary difference between the embodiments depicted in FIGS. 3 and 5 is that the portion 123a of the strut 124a between the secondary bend 126a and the primary bend 122 is not generally parallel to the corresponding portion 123b of the strut 124b. As described with respect to the embodiment of FIG. 3 above, however, formed by the secondary bends 126a and 126b during compression to thereby reduce the maximum bending stresses associated with compression of the stent.

Figure 6:
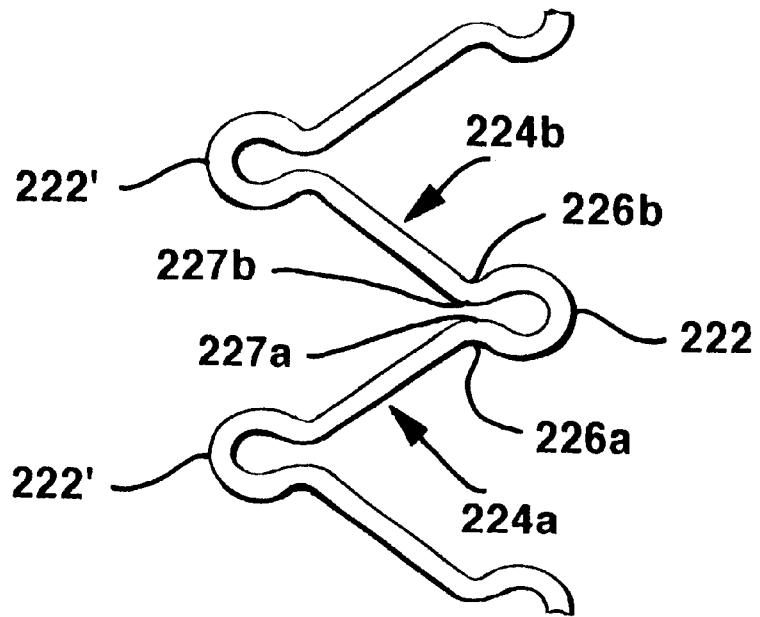

Another alternative construction is depicted in FIG. 6 and includes a primary bend 222 on one end of a support section and two opposing primary bends 222' on the opposing end of the support section. The strut 224a connecting the primary bend 222 with the lower opposing primary bend 222' includes a secondary bend 226a and the strut 224b connecting the primary bend 222 with the upper opposing primary bend 222' includes a secondary bend 226b.

The primary bend 222 in the embodiment of FIG. 6 and the portions of the struts 224a and 224b located between the secondary bends 126a and 126b and the primary bend 222 form a generally circular element as seen in FIG. 6. As described with respect to the embodiments of FIGS. 3 and 5 above, however, it is preferred that the struts 224a and 224b abut first at the apexes 227a and 227b formed by the secondary bends 226a and 226b during compression to thereby reduce the maximum bending stresses associated with compression of the stent.

Figure 7:
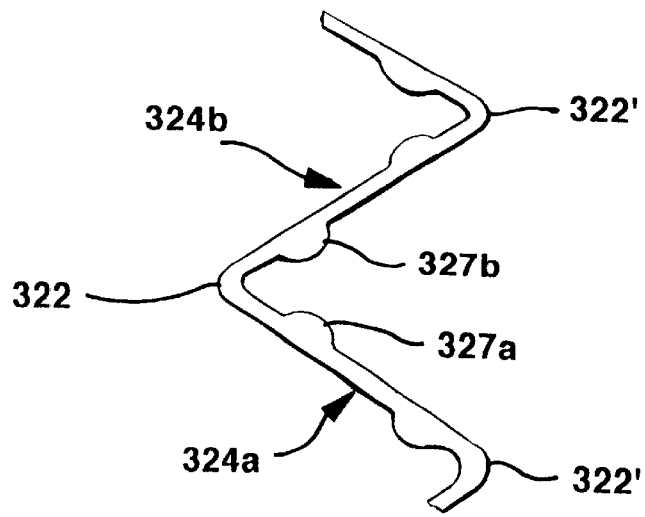

Yet another alternative construction is depicted in FIG. 7 and includes a primary bend 322 on one end of a support section and two opposing primary bends 322' on the opposing end of the support section. The strut 324a connecting the primary bend 322 with the lower opposing primary bend 322' includes a protrusion 327a facing the opposing strut 324b attached to the primary bend 322. Similarly, the strut 324b connecting the primary bend 322 with the upper opposing primary bend 322' includes a protrusion 327b facing the opposing strut 324a.

Although the struts 324a and 324b do not include secondary bends as in those struts described above, the protrusions 327a and 327b define the point at which the struts 324a/324b first abut when the stent is compressed. Because that point is removed from the primary bend 322, the minimum bending radius of the primary bend is limited, thereby reducing the maximum bending stresses at the primary bends that is associated with compression of the stent.

Figure 8:
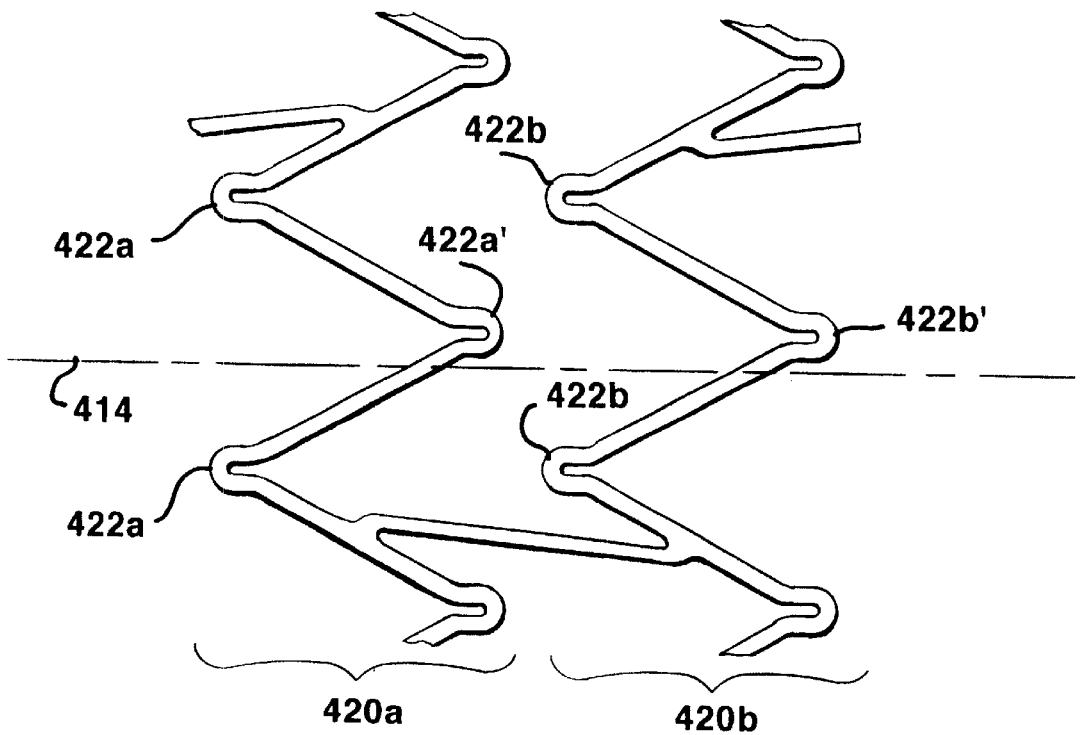

FIG. 8 illustrates yet another feature of stents according to the present invention when compared to the stent depicted in FIG. 2. The view of FIG. 8 is a portion of a stent body including two adjacent support sections 420a and 420b. Support section 420a includes primary bends 422a on one end and opposing primary bends 422a' on the opposite end of the support section 420a. Similarly, the support section 420b includes primary bends 422b on one end of the support section 420b and opposing primary bends 422b' on the opposite end of the support section 420b.

In the embodiment depicted in FIG. 8, the primary bends 422a and 422b in adjacent support sections 420a and 420b are generally aligned along the longitudinal axis 414. Likewise, the primary bends 422a' and 422b' in adjacent support sections 420a and 420b are also generally aligned along the longitudinal axis 414. As a result, the support sections 420a and 420b are said to be "in phase" with each other.

FIG. 2 illustrates a stent in which the support sections 20 are "out of phase" with the adjacent support sections because the primary bends 22 and 22' on the adjacent support sections 20 do not generally align along the longitudinal axis 14 as do the primary bends 422a/422b and 422a'/422b' in the embodiment depicted in FIG. 8.

The radially expandable stents depicted and described above with respect to FIGS. 1–8 are preferably formed as a one-piece, completely integral units from a thin-walled tube of suitable material. Typically, the stents will be cut or machined from a tube using, e.g., laser, water jet, EDM (electrical discharge machining), or chemical etching techniques. As a result, the stents can be formed without welds or joints. It is also envisioned, however, that stents according to the present invention could be formed from a sheet of material using, e.g., laser, water jet, EDM, or chemical etching techniques. If the stent was formed from a sheet of material, the body 10 as seen in FIG. 2 would be formed into a tube and welded or otherwise joined along one side of the stent resulting in a series of welds or other joints along the length of the body.

Preferred materials for stents according to the present invention include those materials that can provide the desired functional characteristics with respect to biological compatibility, modulus of elasticity, etc. For example, it is preferred that the stents be biologically compatible, as well as be capable of significant recoverable strain to assume a low profile for delivery to a desired location within a body lumen. After release of the compressed stent, it is preferred that the stent be capable of radially expanding back to its original diameter.

Particularly preferred materials for stents according to the present invention are nickel titanium alloys and other alloys that exhibit superelastic behavior, i.e., are capable of significant distortion without plastic deformation. Stents manufactured of such materials can be significantly compressed without plastic deformation, i.e., they are compressed such that the maximum strain level in the stent is below the recoverable strain limit of the material. Discussions relating to nickel titanium alloys and other alloys that exhibit behaviors suitable for stents according to the present invention can be found in, e.g., U.S. Pat. No. 5,597,378 (Jervis) and WO 95/31945 (Burmeister et al.). Nickel titanium alloys suitable for use in manufacturing stents according to the present invention can be obtained from, e.g., Memry Corp., Brookfield, Conn.

The radially outward directed force developed by the stents according to the present invention serves two functions. One function is to hold the body lumen open against a force directed radially inward, e.g., a spasm, as well as preventing restriction of the passageway through the lumen by intimal flaps or dissections generated by, e.g., prior balloon angioplasty. Another function is to fix the position of the stent within the body lumen by intimate contact between the stent and the walls of the lumen. The outwardly directed forces must not be excessive, however, to avoid traumatization of the lumen walls by the stent.

The diameters of some preferred stents when in the compressed state for delivery to a desired location within a body lumen is typically reduced from about two to about six times the diameter of the stents when in their expanded state before compression. For example, typical stents may have a compressed external diameter of about 1 millimeter to about 3 millimeters for delivery and an expanded external diameter in a body lumen of about 3 millimeters to about 15 millimeters when released from compression in a large arterial vessel. Some preferred stents used in coronary arteries may have a compressed external diameter of about 1 millimeter and an expanded external diameter in a body lumen of up to about 5 millimeters.

In addition to ranges in diameters, it will also be understood that the stents according to the present invention can have any desired longitudinal length as required for a particular application. Furthermore, although the illustrative stents depicted in FIGS. 1–8 have a plurality of successive support sections, it will be understood that some stents according to the present invention could be manufactured with only one support section (in which case no longitudinal members would be required to connect adjacent support sections).

Figure 9:
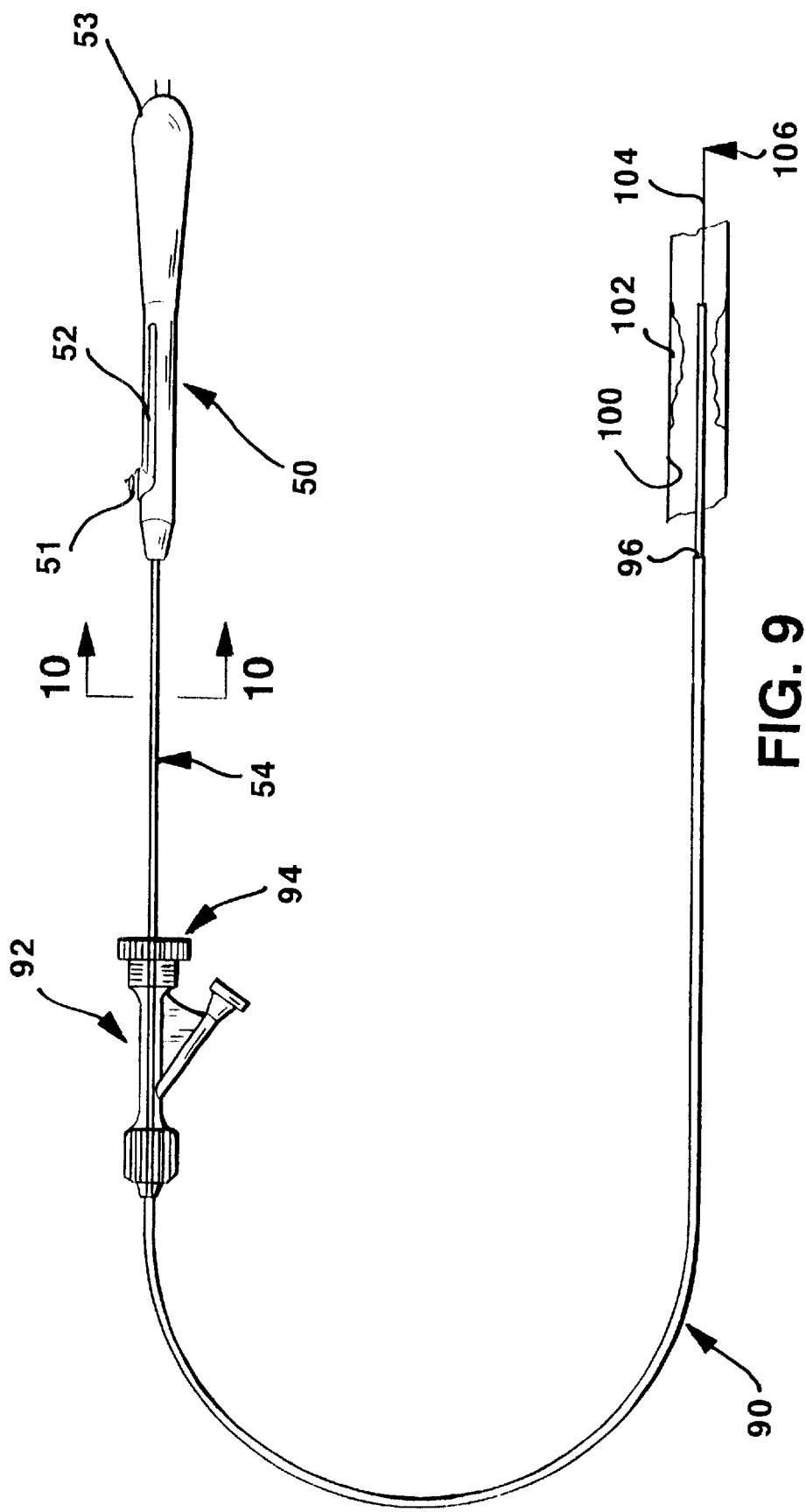
FIG. 9 is a schematic diagram of one delivery system according to the present invention.
Figure 10:
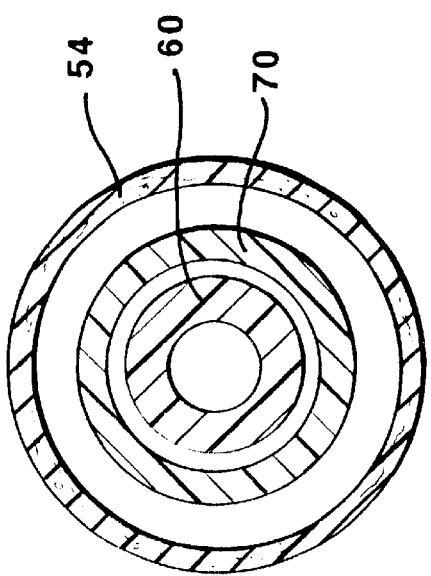
FIG. 10 is an enlarged cross-sectional view of the delivery system of FIG. 9 taken along line 10—10 in FIG. 9.
Figure 11:
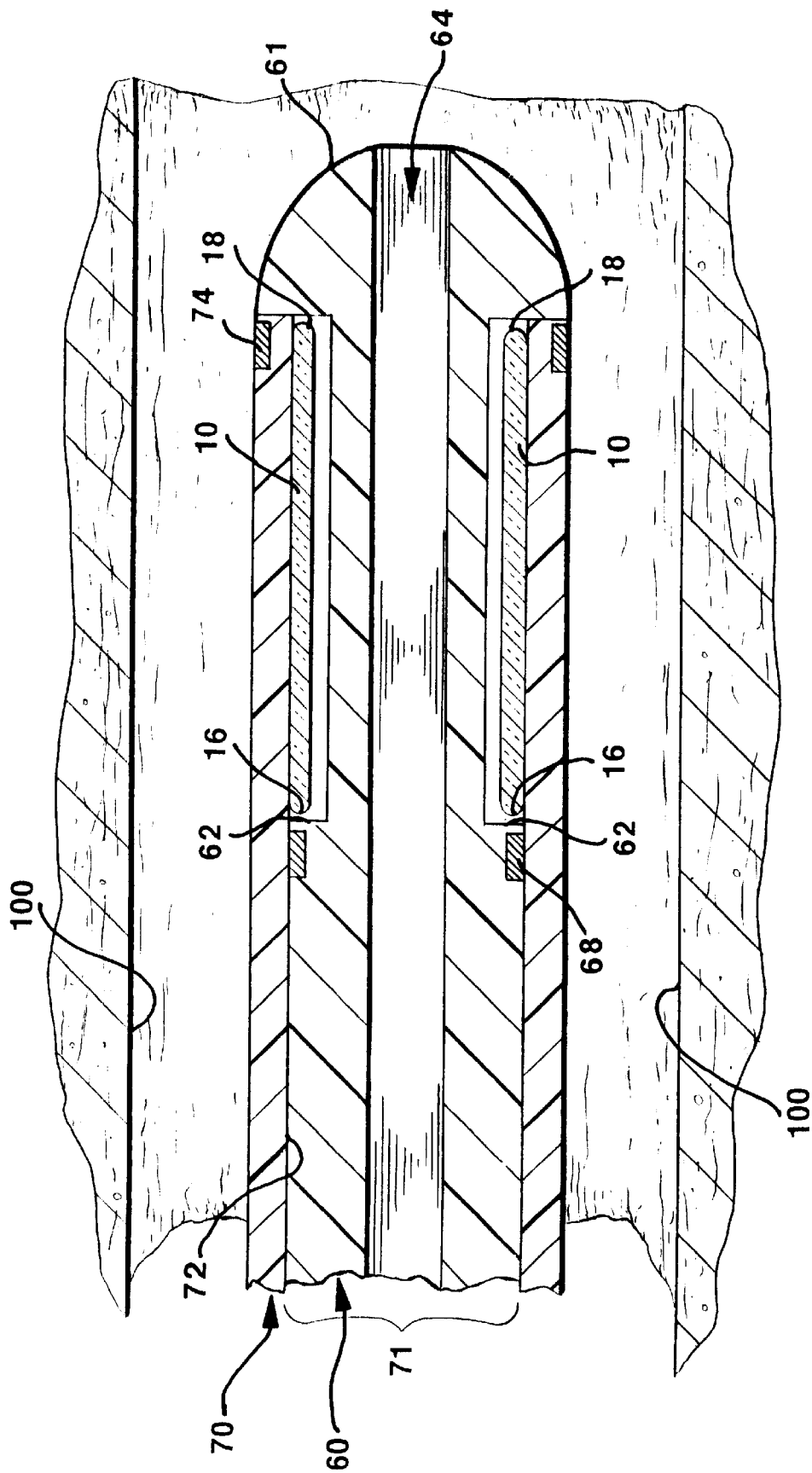
FIG. 11 is an enlarged cross-sectional view of the distal end of the delivery system of FIG. 9.

Having thus described radially expandable stents according to the present invention, we will now describe one delivery system suitable for deploying the self-expanding stents described above as well as other radially expandable stents. The delivery system depicted in FIGS. 9–11 provides for delivery of a stent to a desired location within a body lumen. It will be understood that the stents described above may be deployed by any suitable delivery system and they are not to be limited to deployment by the delivery systems described below.

The delivery system of FIG. 9 includes a handle 50 at the proximal end. The handle 50 includes a release button 51 that slides within a channel 52 located in the handle 50. Preferably, the release button 51 is actuated by a user's thumb to assist in one-handed delivery of the stent as discussed in more detail below.

It is preferred that the release button 51 be locked or retained in position before delivery to prevent accidental or unwanted deployment of the stent from the delivery system. One preferred retaining mechanism is a bend or turn in the distal end of the channel 52 such that the channel 52 includes a circumferential portion at the distal end connecting to the otherwise longitudinal channel 52 seen in FIG. 9. The retaining the release button 51 in position at the distal end of the channel 52 (in the circumferential portion of the channel) until delivery of the stent is desired, at which time the button is moved circumferentially and then longitudinally along the length of the channel 52 to release the stent as discussed in more detail below.

Those skilled in the art will understand that a variety of retaining mechanisms could be substituted for the preferred mechanism described above. Examples of suitable alternatives include, but are not limited to: a removable security band around the handle 50 that must be removed to move the release button 51 proximally, stoppers within the channel 52 that must be removed to move the release button 51 proximally, a detent mechanism in which the release button can be depressed radially inward to release the button 51 for movement within the channel, etc.

A support tube 54 extends from the distal end of the handle 50 and preferably extends into the hemostasis valve 94 of the Y-connector 92 of a guide catheter 90. Preferably, the support tube 54 terminates within the guide catheter 90 at a point near the Y-connector 92. The guide catheter 90 preferably terminates at a distal end 96 spaced from the Y-connector 92. The construction of guide catheters, Y-connectors and hemostasis valves are well known and will not be described further.

FIG. 10 is a cross-sectional view of the proximal portion of the delivery system taken along the longitudinal axis of the support tube 54 as indicated by line 10—10 in FIG. 9. The support tube 54 is coaxial with a cover sheath 70 and inner tube 60, both of which are described in more detail below. It is preferred that the cover sheath 70 be movable within the support tube 54 and that the cover sheath 70 also be movable relative to the inner tube 60. Further, it is preferred that the inner tube 60 and the support tube 54 be fixed relative to each other.

FIG. 11 is an enlarged view of the distal portion of the delivery device in which the stent 10 is located within the lumen 72 formed by the cover sheath 70. The cover sheath 70 maintains the stent 10 in a compressed state in which the stent 10 has a diameter suitable for delivery to an internal body lumen 100. Because the stent 10 is self-expanding, it is biased radially outward against the interior surface of the cover sheath 70 as depicted.

An inner tube 60 preferably extends through the cover sheath 70 and the compressed stent 10 as seen in FIG. 11. The inner tube 60 also preferably includes a guidewire lumen 64 extending through to the distal end 61 of the inner tube 60. For clarity, the guidewire 104 has been removed from the guidewire lumen 64 in the inner tube 60 of FIG. 11.

The preferred inner tube 60 includes a shoulder 62 proximal to the proximal end 16 of the stent 10. The shoulder 62 prevents the stent 10 from moving proximally with the cover sheath 70 during deployment because the outside diameter of the inner tube 60 at the shoulder 62 is greater than the inside diameter of the compressed stent 10.

As a result, the position of the stent 10 relative to the shoulder 62 on inner tube 60 is fixed when the cover sheath 70 is moved proximally during deployment of the stent 10 as described below.

Inner tube 60 preferably extends to the handle 50 of the delivery system depicted in FIG. 9. Furthermore, the inner tube 60 is preferably fixedly attached to the handle 50 and is substantially inextensible along its length. As a result, the distance between the handle 50 and the shoulder 62 on the inner tube 60 is fixed. Because the distance between the shoulder 62 and the handle 50 is fixed, the distance between the handle 50 and the compressed stent 10 on the interior surface of the cover sheath 70 is also fixed during deployment.

The stent 10 is released by moving the cover sheath 70 towards the proximal end of the delivery device, i.e., away from the distal end 61 of the inner tube 60. The cover sheath 70 is connected to an actuator such as a release button 51 on the handle 50 such that movement of the button 51 towards the proximal end 53 of the handle 50 moves the cover sheath 70 in the proximal direction towards the handle 50. If the stent 10 is self-expanding, that movement of the cover sheath 70 preferably removes the constraining forces on the compressed stent 10, thereby allowing it to expand within the lumen 100. Actuators that accomplish the function of moving the cover sheath 70 relative to the handle 50 other than the preferred release button 51 will be known to those skilled in the art.

To assist in positioning the stent 10 during delivery, it is preferred that one radio-opaque marker 68 be provided on the inner tube 60 at the proximal end 16 of the stent 10 and another radio-opaque marker 74 be provided on the cover sheath 70 at the distal end 18 of the stent 10. Movement of the marker 74 on the cover sheath 70 past the marker 68 on the inner tube 60 is preferably indicative of sufficient movement of the cover sheath 70 such that the stent 10 is no longer constrained by within the lumen 72 of the cover sheath has been deployed within the body lumen 100.

Figure 12:
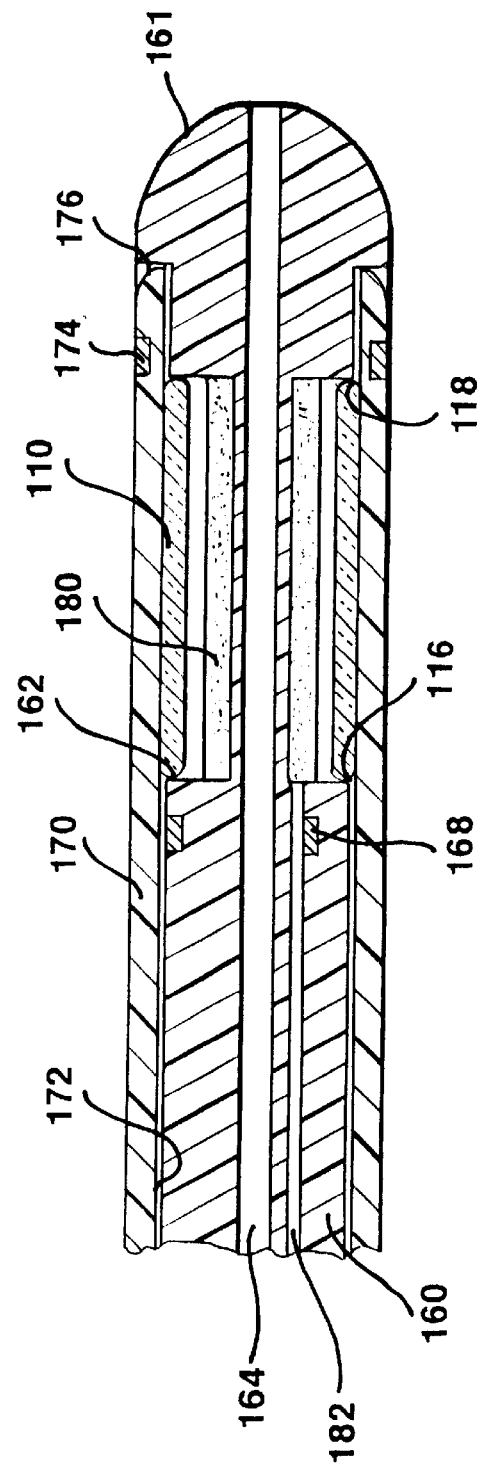
FIG. 12 is an enlarged cross-sectional view of the distal end of an alternate delivery system incorporating a balloon.

FIG. 12 is an enlarged view of the distal portion of an alternative delivery system incorporating an inflatable balloon 180 on the inner tube 160, with the balloon preferably located within the passageway formed by the compressed stent 110. As described in connection with the embodiment depicted in FIG. 11, the stent 110 is located within the lumen 172 formed by the cover sheath 170. The cover sheath 170 maintains the stent 110 in a compressed state in which the stent 110 has a diameter suitable for delivery to an internal body lumen. Because the stent 110 is self-expanding, it is biased radially outward against the interior surface of the cover sheath as depicted.

The inner tube 160 also preferably includes a guidewire lumen 164 extending through to the distal end 161 of the inner tube 160. The inner tube 160 also includes a shoulder 162 at the proximal end 116 of the stent 110 to assist in deploying the stent 110 as described above in connection with FIG. 11. Inner tube 160 also preferably extends to the handle of a delivery system as described above in connection with FIG. 11.

As seen in FIG. 12, the portion of the inner tube 160 on which the balloon 180 is mounted preferably has a reduced diameter to maintain a low profile while allowing room for the balloon 180. The inner tube 160 also includes an inflation lumen 182 in fluid communication with the interior of the collapsed balloon 180. The inflation lumen 182 is used to deliver the fluids used to inflate the balloon 180 during deployment of the stent 110. The inflation lumen 182 preferably terminates at the proximal end of the inner tube 160 where the fluid source can be connected by known methods.

To assist in positioning the stent 110 during delivery, it is preferred that one radio-opaque marker 168 be provided on the inner tube 160 at the proximal end 116 of the stent 110 and another radio-opaque marker 174 be provided on the cover sheath 170 at the distal end 118 of the stent 110. Movement of the marker 174 on the cover sheath 170 past the marker 168 on the inner tube 160 is preferably indicative of sufficient movement of the cover sheath 170 such that the stent 110 is no longer constrained by within the lumen 172 of the cover sheath has been deployed within a body lumen.

As described above in connection with FIG. 9, the preferred delivery systems according to the present invention also preferably include a support tube 54 exterior to and coaxial with the cover sheath 70 and inner tube 60 to further assist in accurate placement of the stent 10. The support tube 54 preferably extends from the handle 50 and is sufficiently long to extend into the lumen of the guide catheter 90. As best seen in FIG. 9, the support tube 54 preferably extends into, e.g., a Y-connector 92 of the guide catheter 90 such that the position of the support tube 54 can be fixed relative to the guide catheter 90 by closure of the hemostasis valve 94 on the Y-connector 92.

It is preferred that the support tube 54 be fixedly attached to the handle 50 and that the support tube 54 be substantially inextensible along its longitudinal axis such that, after the support tube 54 is fixed in the hemostasis valve 94, the handle 50 is located a fixed distance from the hemostasis valve 94. The cover sheath 70 located within the support tube 54 (see FIG. 10) is, however, free to move longitudinally within the support tube 54 during deployment of the stent 10. Because the support tube 54 and the inner tube 60 are both fixedly attached to the handle 50, however, the distance between the stent 10 and the hemostasis valve 94 (and handle 50) are also fixed on closure of the hemostasis valve 94 on the support tube 54.

Use of the delivery system described above will now be described in connection with balloon angioplasty treatment of a lesion within a coronary vessel. Deployment of the stent will typically involve balloon angioplasty to expand the passageway through a lesion. Typically, a balloon catheter will be advanced over a guidewire to the desired location. After dilatation, the balloon catheter will be withdrawn while the guidewire 104 and guide catheter 90 used with the balloon catheter remain in position. The guide catheter 90 is typically sutured in position to fix its location relative to the patient. At that point, the inner tube 60 and cover sheath 70 with compressed stent 10 will be advanced through the guide catheter 90 past the distal end 96 of the guide catheter 90 along the guidewire 104 until the stent 10 is in the desired location relative to the lesion 102. That position can be verified by, e.g., using the radio-opaque markers 68 and 74 on the inner tube 60 and cover sheath 70 as described above.

With the stent 10 in the desired location, the hemostasis valve 94 is preferably fastened or closed on the support tube 54, thereby fixing the position of the stent relative to the guide catheter 90 (which, in turn fixes the position of the stent 10 relative to the patient because of the connection between the guide catheter 90 and the patient as described above). With the hemostasis valve 94 closed, the release button 51 is moved from its locked position within the channel 52 and then gently moved towards the proximal end 53 of the handle 50. That movement preferably draws the distal end 76 of the cover sheath 70 past the stent 10. If the stent 10 is self-expanding, it will typically expand radially outward from the inner tube 60 towards the interior surface of the lesion 102.

After the cover sheath 70 is withdrawn sufficiently to expose the stent 10, the balloon 80 can be inflated to either expand the stent 10 (if it is not self-expanding) or to assist in proper seating of the stent 10 against the interior surface of the lumen 100 and/or lesion 102. The balloon 80 is preferably a high pressure balloon (operating at 12–14 Bars) and preferably has an inflated diameter that is less than or equal to the interior diameter of the stent 10 as expanded.

Figure 13:
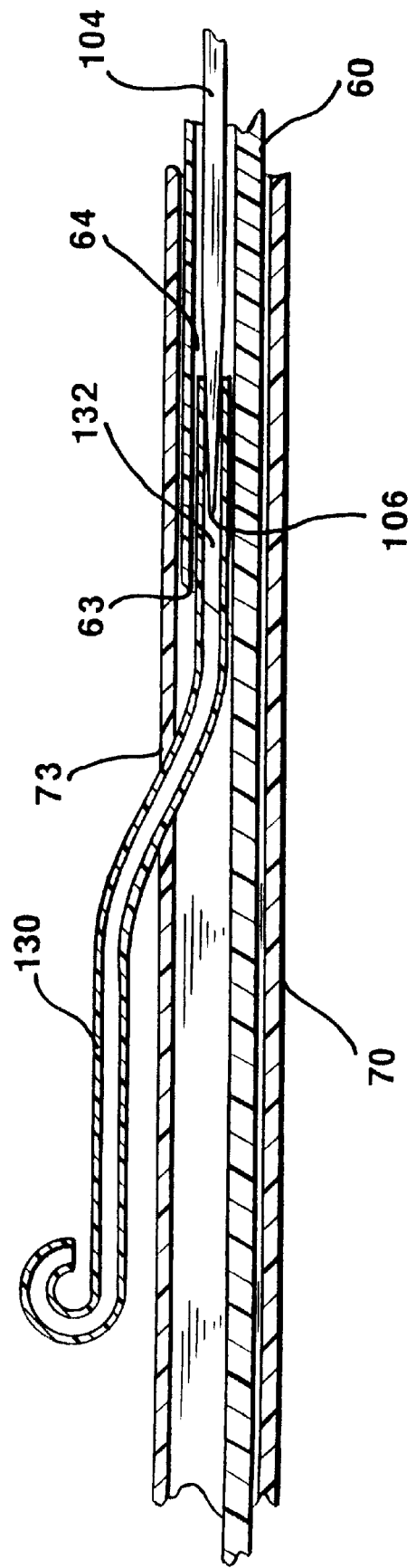
FIG. 13 is an enlarged partial cross-sectional view of one rapid-exchange delivery system according to the present invention.

Another feature of one preferred rapid-exchange delivery system according to the present invention is in the routing of the guidewire 104 out of the inner tube 60 and cover sheath 70 at a point between the distal end 61 of the inner tube 60 and the distal end of the support tube 54. Turning to FIG. 13, a portion of a rapid-exchange delivery system proximal from the distal end 61 of the inner tube 60 is depicted which includes the cover sheath 70 and the inner tube 60 located within the lumen 72 of the cover sheath 70. The guidewire lumen 64 of the inner tube 60 terminates in a first guidewire opening 63 in the depicted embodiment. A second guidewire opening 73 is provided in the cover sheath 70.

A guide element 130 is preferably provided that extends through the second guidewire opening 73 and the first guidewire opening 63 and into the guidewire lumen 64 of the inner tube 60. As such, advancement of the proximal end 106 of the guidewire 104 towards the proximal end of the delivery system through the guidewire lumen 64 (to the left in FIG. 13) moves the proximal end 106 of the guidewire 104 into a lumen 132 in the guide element 130.

It is preferred that only a portion of the guidewire 104 fit within the lumen 132 in the guide element 130. As a result, continued advancement of the guidewire 104 towards the proximal end of the delivery system forces the guide element 130 out of the first and second guidewire openings 63/73 as well as guides the proximal end 106 of the guidewire 104 through those openings. After the proximal end 106 of the guidewire 104 is threaded through the openings 63/73 in the inner tube 60 and cover sheath 70, the distal portion of the inner tube 60 and cover sheath 70 in which the guidewire 104 is contained can be advanced through the guide catheter 90 along the guidewire 104.

Although FIG. 13 illustrates one embodiment of a rapid-exchange delivery system, it will be understood that the stents according to the present invention can be delivered by any delivery system, e.g., an over-the-wire delivery system or by any other suitable delivery system. Furthermore, it will also be understood that the distal portions of the delivery system as depicted in FIGS. 11 and 12 could be used in connection with any suitable delivery system, including, e.g., rapid-exchange or over-the-wire delivery systems.

Furthermore, the preceding specific embodiments are illustrative of the practice of the invention. It is to be understood, however, that other expedients known to those skilled in the art or disclosed herein, may be employed without departing from the scope of the appended claims.

What is claimed is:

1. A self-expanding radially expandable stent for implantation within a body lumen comprising:
    an elongated generally tubular body defining a passageway having a longitudinal axis, the body comprising at least one circumferential support section having a length along the longitudinal axis;
    each of the circumferential support sections comprising a plurality of primary bends interconnected by struts, the primary bends being located on alternating ends of the support section around the circumference of the body, each of the struts connecting successive primary bends on opposite ends of the support section and having a midpoint generally located therebetween;
    wherein the stent is radially compressible into a compressed state and radially self-expanding into an expanded state in which the struts and primary bends in each of the support sections are arranged in a zigzag pattern, and further wherein each pair of adjacent struts associated with each of the primary bends abut at a point between the primary bend and the midpoint of each strut in the pair of adjacent struts when the stent is in the compressed state, whereby bending stress is reduced at each primary bend of the plurality of primary bends.

2. A stent according to claim 1, wherein at least one of the struts in the pair of struts associated with each of the primary bends comprises a secondary bend located between the midpoint and one end of the strut, the secondary bend including an apex facing the other strut in the pair of struts, and further wherein the point at which the pair of struts abut is at the apex of the secondary bend when the stent is in the compressed state.

3. A stent according to claim 1, wherein each strut of the plurality of struts comprises two secondary bends, one of the secondary bends located on each side of the midpoint of the strut and each of the secondary bends being spaced from the ends of the strut, each of the secondary bends having an apex, wherein the apexes of each of the secondary bends face the opposing struts in each pair of struts associated with one of the primary bends in the support section, and further wherein the point at which each pair of struts associated with one of the primary bends abut when the stent is in the compressed state is at the apexes of the secondary bends of the struts.

4. A stent according to claim 1, wherein at least one of the struts in each pair of struts associated with one of the primary bends comprises a protrusion located between the midpoint and one end of the strut, the protrusion facing the other strut in the pair of struts, and further wherein the point at which the pair of struts abut is at the protrusion when the stent is in the compressed state.

5. A stent according to claim 1, wherein each strut of the plurality of struts comprises two protrusions, one of the protrusions located on each side of the midpoint of the strut and each of the protrusions being spaced from the ends of the strut, wherein the protrusions face the opposing struts in each pair of struts associated with one of the primary bends in the support section, and further wherein the point at which each pair of struts associated with one of the primary bends abut when the stent is in the compressed state is at the protrusions in the struts.

6. A stent according to claim 1, wherein all of the support sections are in phase with each other.

7. A stent according to claim 1, wherein at least one pair of adjacent support sections are out of phase with each other.

8. A self-expanding radially expandable stent for implantation within a body lumen comprising:
    an elongated generally tubular body defining a passageway having a longitudinal axis, the body comprising at least one circumferential support section having a length along the longitudinal axis;
    each of the circumferential support sections comprising a substantially continuous element including a plurality of primary bends interconnected by struts, the primary bends being located on alternating ends of the support section around the circumference of the body, each of the struts connecting successive primary bends on opposite ends of the support section and having a midpoint generally located therebetween, wherein the stent is radially compressible into a compressed state and radially self-expanding into an expanded state in which the struts and primary bends in each of the support sections are arranged in a zigzag pattern; and means for reducing bending stress at the primary bends when the stent is in the compressed state, wherein the means for reducing bending stress causes each pair of struts associated with one of the primary bends to abut at a point between the midpoints of the pair of struts and the primary bend.

9. A stent according to claim 8, wherein the body comprises a plurality of circumferential support sections arranged successively along the longitudinal axis, and further wherein the body comprises at least one longitudinal member connecting adjacent support sections in the body, the longitudinal member having a first end attached to one of the support sections and a second end attached to the adjacent support section.

10. A stent according to claim 9, wherein the first end of each of the longitudinal members is attached proximate the midpoint of one of the struts in one of the support sections and the second end of each of the longitudinal members is attached proximate the midpoint of one of the struts in an adjacent support section; wherein the longitudinal length of the stent in the compressed state is substantially the same as the longitudinal length of the stent in the expanded state.

11. A radially expandable stent for implantation within a body lumen comprising:

an elongated generally tubular body defining a passageway having a longitudinal axis;

the body comprising a plurality of circumferential support sections arranged successively along the longitudinal axis, each of the support sections having a length along the longitudinal axis;

each of the circumferential support sections comprising a plurality of primary bends interconnected by struts, the primary bends being located on alternating ends of the support section around the circumference of the body, each of the struts connecting successive primary bends on opposite ends of the support section and having a midpoint generally located therebetween, wherein each primary bend of the plurality of primary bends connects a pair of struts in the support section, and further wherein each pair of struts abut at a point between the primary bend and the midpoint of each of the struts in the pair of struts when the stent is in a compressed state, whereby bending stress is reduced at each primary bend of the plurality of primary bends, and still further wherein at least one of the struts in each pair of struts associated with one of the primary bends comprises a secondary bend located between the midpoint and one end of the strut, the secondary bend including an apex facing the other strut in the pair of struts, and further wherein the point at which the pair of struts abut is at the apex of the secondary bend when the stent is in the compressed state; and at least one longitudinal member connecting adjacent support sections in the body, the longitudinal member having a first end attached proximate the midpoint of one of the struts and a second end attached proximate the midpoint of one of the struts in the adjacent support section;

wherein the stent is radially compressible into the compressed state in which the struts are generally aligned with the longitudinal axis and radially expandable into an expanded state in which the struts and the primary bends in each of the support sections are arranged in a zigzag pattern, and further wherein the longitudinal length of the stent in the compressed state is substantially the same as the longitudinal length of the stent in the expanded state.

12. A radially expandable stent for implantation within a body lumen comprising:

an elongated generally tubular body defining a passageway having a longitudinal axis;

the body comprising a plurality of circumferential support sections arranged successively along the longitudinal axis, each of the support sections having a length along the longitudinal axis;

each of the circumferential support sections comprising a plurality of primary bends interconnected by struts, the primary bends being located on alternating ends of the support section around the circumference of the body, each of the struts connecting successive primary bends on opposite ends of the support section and having a midpoint generally located therebetween, wherein each primary bend of the plurality of primary bends connects a pair of struts in the support section, and further wherein each pair of struts abut at a point between the primary bend and the midpoint of each of the struts in the pair of struts when the stent is in a compressed state, whereby bending stress is reduced at each primary bend of the plurality of primary bends, and still further wherein each strut of the plurality of struts comprises two secondary bends, one of the secondary bends located on each side of the midpoint of the strut and each of the secondary bends being spaced from the ends of the strut, each of the secondary bends having an apex, wherein the apexes of each of the secondary bends face the opposing struts in each pair of struts associated with one of the primary bends in the support section, and further wherein the point at which each pair of struts associated with one of the primary bends abut when the stent is in the compressed state is at the apexes of the secondary bends of the struts; and at least one longitudinal member connecting adjacent support sections in the body, the longitudinal member having a first end attached proximate the midpoint of one of the struts and a second end attached proximate the midpoint of one of the struts in the adjacent support section;

wherein the stent is radially compressible into the compressed state in which the struts are generally aligned with the longitudinal axis and radially expandable into an expanded state in which the struts and the primary bends in each of the support sections are arranged in a zigzag pattern, and further wherein the longitudinal length of the stent in the compressed state is substantially the same as the longitudinal length of the stent in the expanded state.

13. A radially expandable stent for implantation within a body lumen comprising:

an elongated generally tubular body defining a passageway having a longitudinal axis;

the body comprising a plurality of circumferential support sections arranged successively along the longitudinal axis, each of the support sections having a length along the longitudinal axis;

each of the circumferential support sections comprising a plurality of primary bends interconnected by struts, the primary bends being located on alternating ends of the support section around the circumference of the body, each of the struts connecting successive primary bends on opposite ends of the support section and having a midpoint generally located therebetween, wherein each primary bend of the plurality of primary bends connects a pair of struts in the support section, and further wherein each pair of struts abut at a point between the primary bend and the midpoint of each of the struts in the pair of struts when the stent is in a compressed state, whereby bending stress is reduced at each primary bend of the plurality of primary bends, and still further wherein at least one of the struts in each pair of struts associated with one of the primary bends comprises a protrusion located between the midpoint and one end of the strut, the protrusion facing the other strut in the pair of struts, and further wherein the point at which the pair of struts abut is at the protrusion when the stent is in the compressed state; and at least one longitudinal member connecting adjacent support sections in the body, the longitudinal member having a first end attached proximate the midpoint of one of the struts and a second end attached proximate the midpoint of one of the struts in the adjacent support section;

wherein the stent is radially compressible into the compressed state in which the struts are generally aligned with the longitudinal axis and radially expandable into an expanded state in which the struts and the primary bends in each of the support sections are arranged in a zigzag pattern, and further wherein the longitudinal length of the stent in the compressed state is substantially the same as the longitudinal length of the stent in the expanded state.

14. A radially expandable stent for implantation within a body lumen comprising:

an elongated generally tubular body defining a passageway having a longitudinal axis;

the body comprising a plurality of circumferential support sections arranged successively along the longitudinal axis, each of the support sections having a length along the longitudinal axis;

each of the circumferential support sections comprising a plurality of primary bends interconnected by struts, the primary bends being located on alternating ends of the support section around the circumference of the body, each of the struts connecting successive primary bends on opposite ends of the support section and having a midpoint generally located therebetween, wherein each primary bend of the plurality of primary bends connects a pair of struts in the support section, and further wherein each pair of struts abut at a point between the primary bend and the midpoint of each of the struts in the pair of struts when the stent is in a compressed state, whereby bending stress is reduced at each primary bend of the plurality of primary bends, and still further wherein each strut of the plurality of struts comprises two protrusions, one of the protrusions located on each side of the midpoint of the strut and each of the protrusions being spaced from the ends of the strut, wherein the protrusions face the opposing struts in each pair of struts associated with one of the primary bends in the support section, and further wherein the point at which each pair of struts abut when the stent is in the compressed state is at the protrusions in each strut in the pair of adjacent struts; and at least one longitudinal member connecting adjacent support sections in the body, the longitudinal member having a first end attached proximate the midpoint of one of the struts and a second end attached proximate the midpoint of one of the struts in the adjacent support section;

wherein the stent is radially compressible into the compressed state in which the struts are generally aligned with the longitudinal axis and radially expandable into an expanded state in which the struts and the primary bends in each of the support sections are arranged in a zigzag pattern, and further wherein the longitudinal length of the stent in the compressed state is substantially the same as the longitudinal length of the stent in the expanded state.

* * * * *

UNITED STATES PATENT AND TRADEMARK OFFICE
CERTIFICATE OF CORRECTION

PATENT NO. : 6,533,807 B2  Page 1 of 1
DATED : March 18, 2003
INVENTOR(S) : Wolinsky et al.

It is certified that error appears in the above-identified patent and that said Letters Patent is hereby corrected as shown below:

Title page,
Item [56], FOREIGN PATENT DOCUMENTS, please delete "WO 9626689 *6/1996" and insert -- WO 96/26689 *9/1996 --.

Column 9,
Line 48, please insert after the word "however," the following: -- it is preferred that the struts 124a and 124b abut first at the apexes 127a and 127b --.

Signed and Sealed this

Fourteenth Day of October, 2003

JAMES E. ROGAN
*Director of the United States Patent and Trademark Office*